US006520376B2

(12) United States Patent
Verdone

(10) Patent No.: US 6,520,376 B2
(45) Date of Patent: Feb. 18, 2003

(54) HIGH VOLUME EVACUATION TIP HOLDING AND DISPENSING APPARATUS

(76) Inventor: Kristen Verdone, 333 First St., #D-210, Seal Beach, CA (US) 90740

( * ) Notice: Subject to any disclaimer, the term of this patent is extended or adjusted under 35 U.S.C. 154(b) by 55 days.

(21) Appl. No.: 09/844,608

(22) Filed: Apr. 27, 2001

(65) Prior Publication Data

US 2002/0158077 A1 Oct. 31, 2002

(51) Int. Cl.$^7$ ................................................. B23Q 7/04
(52) U.S. Cl. ...................................... 221/208; 206/467
(58) Field of Search ............................ 221/208, 9, 256, 221/257, 255, 268; 206/461, 467, 361, 362

(56) References Cited

U.S. PATENT DOCUMENTS 4,236,637 A * 12/1980 Castner et al. .............. 206/362

* cited by examiner

Primary Examiner—Kenneth W. Noland
(74) Attorney, Agent, or Firm—Goldstein & Lavas, P.C.

(57) ABSTRACT

A high volume evacuation tip holding and dispensing apparatus including a housing dimensioned for holding a plurality of disposable high volume evacuation tips therein in a horizontal orientation. The housing has a dispensing channel depending therefrom. The dispensing channel has an open upper end in communication with a hollow interior of the housing, and an open lower end. A collection tray is secured to the open lower end of the dispensing channel of the housing for holding a single disposable high volume evacuation tip thereon. A dispensing block is slidably disposed within the hollow interior of the housing above the open upper end of the dispensing channel to allow passage of a single disposable high volume evacuation tip into the dispensing channel for passage into the collection tray.

4 Claims, 1 Drawing Sheet

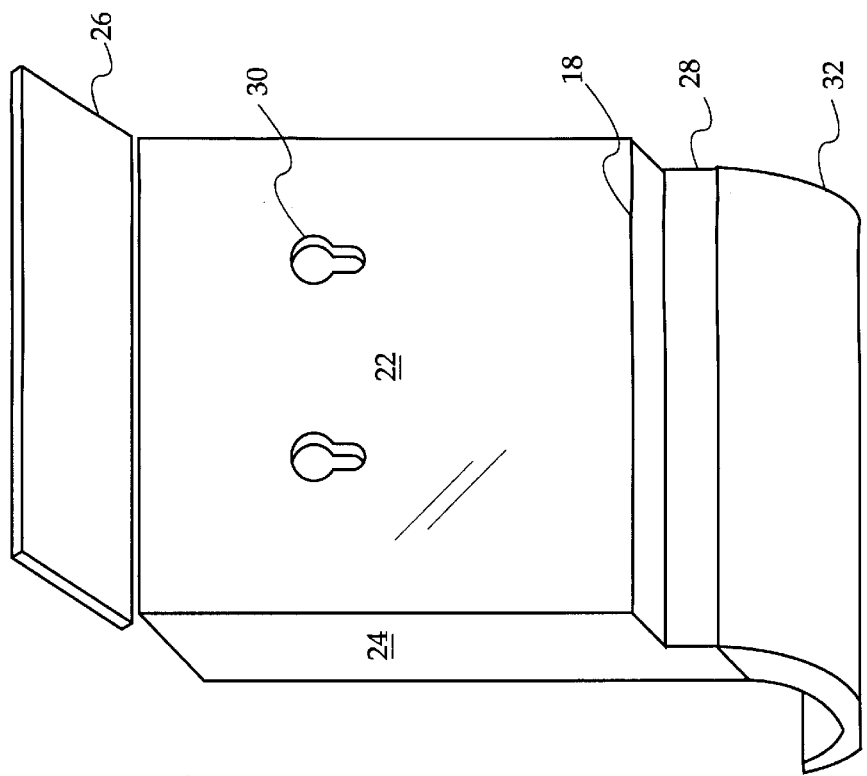
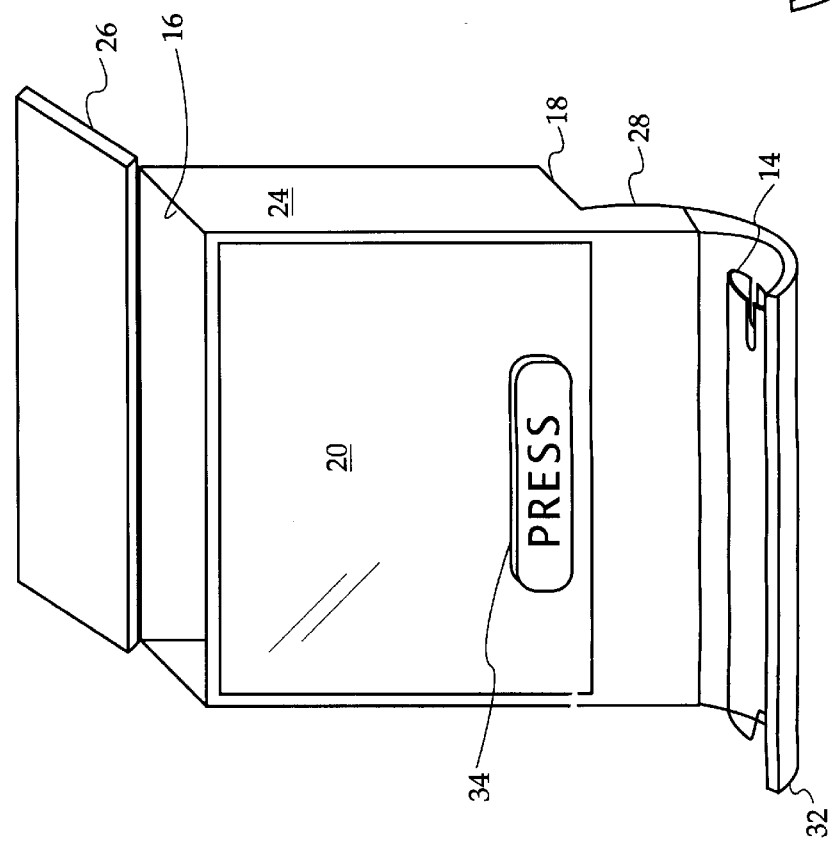

HIGH VOLUME EVACUATION TIP HOLDING AND DISPENSING APPARATUS

BACKGROUND OF THE INVENTION

The present invention relates to a high volume evacuation tip holding and dispensing apparatus and more particularly pertains to holding a quantity of high volume evacuation tips for easy dispensing.

The use of storage and dispensing devices is known in the prior art. More specifically, storage and dispensing devices heretofore devised and utilized for the purpose of storing and dispensing selected items are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,236,637 to Castner, Sr. discloses a storage dispenser for cotton swabs through a bottom door assembly. U.S. Pat. Nos. 5,163,561 to Fitzgerald and 5,692,609 to Lin disclose various dental equipment storage containers. U.S. Pat. No. 4,580,978 to Motola discloses a dental high volume evacuation system.

While these devices fulfill their respective, particular objective and requirements, the aforementioned patents do not describe a high volume evacuation tip holding and dispensing apparatus for holding a quantity of high volume evacuation tips for easy dispensing.

In this respect, the high volume evacuation tip holding and dispensing apparatus according to the present invention substantially departs from the conventional concepts and designs of the prior art, and in doing so provides an apparatus primarily developed for the purpose of holding a quantity of high volume evacuation tips for easy dispensing.

Therefore, it can be appreciated that there exists a continuing need for a new and improved high volume evacuation tip holding and dispensing apparatus which can be used for holding a quantity of high volume evacuation tips for easy dispensing. In this regard, the present invention substantially fulfills this need.

SUMMARY OF THE INVENTION

In the view of the foregoing disadvantages inherent in the known types of storage and dispensing devices now present in the prior art, the present invention provides an improved high volume evacuation tip holding and dispensing apparatus. As such, the general purpose of the present invention, which will be described subsequently in greater detail, is to provide a new and improved high volume evacuation tip holding and dispensing apparatus which has all the advantages of the prior art and none of the disadvantages.

To attain this, the present invention essentially comprises a housing dimensioned for holding a plurality of disposable high volume evacuation tips therein in a horizontal orientation. The housing has a generally rectangular configuration defined by an open upper end, a closed lower end, a front wall, a back wall, and opposed side walls defining a hollow interior. The open upper end has a lid hingedly secured thereto. The closed lower end has a dispensing channel depending therefrom. The dispensing channel has an open upper end in communication with the hollow interior, and an open lower end. The back wall has a pair of mounting apertures formed therein. A collection tray is secured to the open lower end of the dispensing channel of the housing. The collection tray has an arcuate cross-section dimensioned for holding a single disposable high volume evacuation tip thereon. A dispensing block is slidably disposed within the hollow interior of the housing above the open upper end of the dispensing channel. The dispensing block has an outer portion extending outwardly of the front wall of the housing whereby inward pressing of the dispensing block will allow passage of a single disposable high volume evacuation tip into the dispensing channel for passage into the collection tray.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved high volume evacuation tip holding and dispensing apparatus which has all the advantages of the prior art storage and dispensing devices and none of the disadvantages.

It is another object of the present invention to provide a new and improved high volume evacuation tip holding and dispensing apparatus which may be easily and efficiently manufactured and marketed.

It is a further object of the present invention to provide a new and improved high volume evacuation tip holding and dispensing apparatus which is of durable and reliable construction.

An even further object of the present invention is to provide a new and improved high volume evacuation tip holding and dispensing apparatus which is susceptible of a low cost of manufacture with regard to both materials and labor, and which accordingly is then susceptible of low prices of sale to the consuming public, thereby making such a high volume evacuation tip holding and dispensing apparatus economically available to the buying public.

Even still another object of the present invention is to provide a new and improved high volume evacuation tip holding and dispensing apparatus for holding a quantity of high volume evacuation tips for easy dispensing.

Lastly, it is an object of the present invention to provide a new and improved high volume evacuation tip holding and dispensing apparatus including a housing dimensioned for holding a plurality of disposable high volume evacuation tips therein in a horizontal orientation. The housing has a dispensing channel depending therefrom. The dispensing channel has an open upper end in communication with a hollow interior of the housing, and an open lower end. A collection tray is secured to the open lower end of the dispensing channel of the housing for holding a single disposable high volume evacuation tip thereon. A dispensing block is slidably disposed within the hollow interior of the housing above the open upper end of the dispensing channel to allow passage of a single disposable high volume evacuation tip into the dispensing channel for passage into the collection tray.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the high volume evacuation tip holding and dispensing apparatus constructed in accordance with the principles of the present invention.

FIG. 2 is a rear perspective view of the present invention.

FIG. 3 is a side view of a disposable high volume evacuation tip of the present invention.

The same reference numerals refer to the same parts through the various figures.

DESCRIPTION OF THE PREFERRED EMBODIMENT

With reference now to the drawings, and in particular, to FIGS. 1 through three thereof, the preferred embodiment of the new and improved high volume evacuation tip holding and dispensing apparatus embodying the principles and concepts of the present invention and generally designated by the reference number 10 will be described.

Specifically, it will be noted in the various Figures that the device relates to a high volume evacuation tip holding and dispensing apparatus for holding a quantity of high volume evacuation tips for easy dispensing. In its broadest context, the device consists of a housing, a collection tray, and a dispensing block. Such components are individually configured and correlated with respect to each other so as to attain the desired objective.

The housing 12 is dimensioned for holding a plurality of disposable high volume evacuation tips 14 therein in a horizontal orientation. The disposable high volume evacuation tips 14 are connected to aspiration nozzles that are used to extract liquid and dental debris which is produced during a dental procedure. The tips 14 are designed for single use after which they are properly discarded. The housing 12 has a generally rectangular configuration defined by an open upper end 16, a closed lower end 18, a front wall 20, a back wall 22, and opposed side walls 24 defining a hollow interior. The open upper end 16 has a lid 26 hingedly secured thereto. The lid 26 can be easily raised to add disposable high volume evacuation tips 14 to the housing 12 when needed. The closed lower end 18 has a dispensing channel 28 depending therefrom. The dispensing channel 28 has an open upper end in communication with the hollow interior, and an open lower end. The back wall 22 has a pair of mounting apertures 30 formed therein. The mounting apertures 30 are essentially key holes that will allow the housing 12 to be mounted on a wall or other recipient surface.

The collection tray 32 is secured to the open lower end of the dispensing channel 28 of the housing 12. The collection tray 32 has an arcuate cross-section dimensioned for holding a single disposable high volume evacuation tip 14 thereon.

The dispensing block 34 is slidably disposed within the hollow interior of the housing 12 above the open upper end of the dispensing channel 28. The dispensing block 34 has an outer portion extending outwardly of the front wall 20 of the housing 12 whereby inward pressing of the dispensing block 34 will allow passage of a single disposable high volume evacuation tip 14 into the dispensing channel 28 for passage into the collection tray 32.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A high volume evacuation tip holding and dispensing apparatus for holding a quantity of high volume evacuation tips for easy dispensing comprising, in combination:

a housing dimensioned for holding a plurality of disposable high volume evacuation tips therein in a horizontal orientation, the housing having a generally rectangular configuration defined by an open upper end, a closed lower end, a front wall, a back wall, and opposed side walls defining a hollow interior, the open upper end having a lid hingedly secured thereto, the closed lower end having a dispensing channel depending therefrom, the dispensing channel having an open upper end in communication with the hollow interior, and an open lower end, the back wall having a pair of mounting apertures formed therein;

a collection tray secured to the open lower end of the dispensing channel of the housing, the collection tray having an arcuate cross-section dimensioned for holding a single disposable high volume evacuation tip thereon; and a dispensing block slidably disposed within the hollow interior of the housing above the open upper end of the dispensing channel, the dispensing block having an outer portion extending outwardly of the front wall of the housing whereby inward pressing of the dispensing block will allow passage of a single disposable high volume evacuation tip into the dispensing channel for passage into the collection tray.

2. A high volume evacuation tip holding and dispensing apparatus for holding a quantity of high volume evacuation tips for easy dispensing comprising, in combination:

a housing dimensioned for holding a plurality of disposable high volume evacuation tips therein in a horizontal orientation, the housing having a dispensing channel depending therefrom, the dispensing channel having an open upper end in communication with a hollow interior of the housing, and an open lower end, the housing further having an open upper end having a lid hingedly secured thereto;

a collection tray secured to the open lower end of the dispensing channel of the housing for holding a single disposable high volume evacuation tip thereon; and a dispensing block slidably disposed within the hollow interior of the housing to allow passage of a single disposable high volume evacuation tip into the dispensing channel for passage into the collection tray.

3. The high volume evacuation tip holding and dispensing apparatus as set forth in claim two, wherein the collection tray has an arcuate cross-section.

4. The high volume evacuation tip holding and dispensing apparatus as set forth in claim two, wherein the dispensing block has an outer portion extending outwardly of a front wall of the housing whereby inward pressing of the dispensing block will allow passage of a single disposable high volume evacuation tip into the dispensing channel for passage into the collection tray.

* * * * *